US005744477A

United States Patent [19]
Cincotta et al.

[11] Patent Number: 5,744,477
[45] Date of Patent: Apr. 28, 1998

[54] METHOD FOR TREATMENT OF OBESITY USING PROLACTIN MODULATORS AND DIET

[75] Inventors: Anthony H. Cincotta; Albert H. Meier, both of Andover, Mass.

[73] Assignees: The Board of Supervisors of Louisiana State University and Agricultural and Mechanical College, Baton Rouge, La.; Ergo Research Corporation, Walkefield, R.I.

[21] Appl. No.: 178,569

[22] Filed: Jan. 7, 1994

Related U.S. Application Data

[63] Continuation-in-part of Ser. No. 995,292, Dec. 22, 1992, Pat. No. 5,585,347, which is a continuation-in-part of Ser. No. 719,745, Jun. 24, 1991, Pat. No. 5,344,832, which is a continuation-in-part of Ser. No. 463,327, Jan. 10, 1990, abandoned, which is a continuation-in-part of Ser. No. 192,332, May 10, 1988, abandoned.

[51] Int. Cl.⁶ .................................................. A61K 31/44
[52] U.S. Cl. .......................................... 514/288; 514/909
[58] Field of Search ................................ 514/288, 909

[56] References Cited

U.S. PATENT DOCUMENTS

| | | | |
|---|---|---|---|
| 4,219,555 | 8/1980 | Rucman | 514/250 |
| 4,239,763 | 12/1980 | Milavec | 514/250 |
| 4,659,715 | 4/1987 | Meier | 514/288 |
| 4,749,709 | 6/1988 | Meier | 514/288 |
| 4,783,469 | 11/1988 | Meier | 514/288 |
| 5,006,526 | 4/1991 | Meier | 514/250 |
| 5,344,832 | 9/1994 | Cincotta et al. | 514/288 |
| 5,585,347 | 12/1996 | Meier et al. | 514/12 |

FOREIGN PATENT DOCUMENTS

| | | |
|---|---|---|
| BE-890-369 | 9/1980 | Japan . |
| PCT/US92/05074 | 6/1992 | WIPO . |
| PCT/US92/11166 | 12/1992 | WIPO . |

OTHER PUBLICATIONS

Barnett et al., *Postgraduate Med. J.* 56:11–14, 1980.
Bartness et al., *J. Exp. Zoology* 244:437–454, 1987.
Berle, *Acta endocr. Suppl.* 173, Abstract No. 104, 1973.
Burns, et al., *Rev. Chronopharmacology* 5:57–60, 1988.
Chemical Abstracts, vol. 109, No. 9, 66888w, Aug. 29, 1988.
Cincotta et al.,*Amer. J. of Physiol.* 285–93, Feb. 1993.
Cincotta et al., *Life Sciences* 45:2247–2254, 1989.
Cincotta et al., *Ann Nutr Metab* 33:305–14, 1989.
Cincotta et al., *Horm. Metabol. Res.* 21:64–68, 1989.
Cincotta et al., *J. Endocrinology* 120:385–391, 1989.
Cincotta et al., *Experientia* 43:416–417, 1987.
Cincotta et al., *J. Endocr.* 106:177–181, 1985.
Cincotta et al., *J. Endocr.* 106:173–176, 1985.
Cincotta et al., *J. Endocr.* 103:141–146, 1984.
Eisemann et al., *J. of Animal Sci.* 59(1)95–104, 1984.
Eisemann et al., *J. of Animal Sci.* 59(1)86–94, 1984.
Gnudi et al., *Acta Diabetologica Latina* 14:119–128, 1977.
Horseman et al., *J. Endocr.* 82:367–372, 1979.

Horseman et al., *General and Comparative Endocrinology* 38:269–274, 1979.
Joseph et al., *J. Exp. Zool.* 178(1):59–62, 1971.
Landgraf et al., *Proc. German Med. Soc.* 82nd Convention, Part II, Apr. 25–29, 1976.
Lee et al., *J. of Exp. Zool.* 166(3):307–316, 1969.
Meier et al., *Nature* 271:469–471, 1978.
Meier, et al., *Experientia* 48:248–253, 1992.
Meier, *Amer. Zoology,* 15:905–916, 1975.
Meier, *Amer. Scientist* 61(2)184–187, 1973.
Meier, *Gen. & Comp. Endocrin. Supp.* 2:55–62, 1969.
Meier et al.,*Gen. & Comp. Endocrin.* 8(1):110–114, 1967.
Meier et al.,*Compar. Endocrin.* 141–44, 1978.
Meier et al., *Amer. J. of Physiology* 232(2):E193–E196, 1977.
Meier et al., *Amer. Zool.* 16:649–659, 1976.
Southern et al., *J. Anim. Sci.* 68:931–936, 1990.
Spieler et al., *Gen. & Comparative Endocrinology* 29:156–160, 1976.
Spieler et al., *Life Sciences* 22:255–258, 1977.
Thomas et al., *Semaine des Hopitaux de Paris* 53(34–35):1857–1862, 1977.
Wheeland, et al., *Comp. Biochem. Physiol.* vol. 53B; 379–385, 1976.
Wilson et al., *Chronobiology Int'l* 6(2):113–121, 1989.3:189–195, 1989.
Meier et al., *Science* 173: 1240–42, 1971.
Meier et al., *Gen. & Comp. Endocrin.* 17: 311–8, 1971.
Martin et al., *Neuroendocrinology* 52: 9–14, 1990.
Martin et al., *The Condor* 75: 369–374, 1973.
Cassar, J. et al. "Bromocriptine Treatment of Acromegaly," *Metabolism* 26: 539–546 (1977).
Dolocek, R. et al. "Bromocriptine and glucose tolerance in acromegalics," *Pharmatherapeutica* 3: 100–106 (1982).
Eskildsen, P.C. et al. "Long–Term Treatment of Acromegaly with Bromocriptine," *Acta Endocr.* 87: 687–700 (1978).
Steinbeck, K. and J.R. Turtle, "Treatment of Acromegaly-with Bromocryptine," *Aust. N.Z. J. Med.*9: 217–224 (1979).
Wass, J.A.H. et al. "An Assessment of Glucose Intolerance In Acromegaly and Its Response to Medical Treatment," *Clin. Endocr.* 12: 53–59 (1980).

*Primary Examiner*—Kevin E. Weddington
*Attorney, Agent, or Firm*—Darby & Darby

[57] ABSTRACT

The present invention is directed to an improvement in a method of weight and/or body-fat reduction comprising a (preferably moderate) reduction in the caloric intake of a subject in need of such treatment in combination with administration to said subject of a prolactin inhibitor. Additionally, the present invention is directed to an improvement in a method for altering and/or resetting prolactin profiles (and thereby controlling one or more metabolic disorders such as obesity, excessive body fat, hyperlipidemia, hyperlipoproteinemia, hyperglycemia, hypercholesterolemia, hyperinsulinemia, insulin resistance, glucose intolerance, and Type II diabetes) comprising administration to a subject in need of such treatment of a prolactin inhibitor at a predetermined time or times during a 24-hour period in combination with a (preferably moderate) reduction of the caloric intake of said subject.

32 Claims, 2 Drawing Sheets

METHOD FOR TREATMENT OF OBESITY USING PROLACTIN MODULATORS AND DIET

RELATED APPLICATIONS

This application is a continuation-in-part of U.S. application Ser. No. 07/995,292 filed Dec. 22, 1992, U.S. Pat. No. 5,585,347, in turn a continuation-in-part of U.S. application Ser. No. 07/719,745 filed Jun. 24, 1991, U.S. Pat. No. 5,344,832, in turn a continuation-in-part of Ser. No. 463,327, filed Jan. 10, 1990, now abandoned, which is a continuation-in-part of Ser. No. 192,332 filed May 10, 1988, now abandoned, all by Anthony H. Cincotta and Albert H. Meier.

FIELD OF THE INVENTION

This invention relates to an improved method for the reduction in a subject, vertebrate animal or human, of weight and/or body fat stores. This method involves a reduction in caloric intake, in combination with the administration of a prolactin inhibitor.

In another aspect, this invention relates to an improved method for altering and/or resetting prolactin profiles of a vertebrate subject (including a human), by administering to such subjects a prolactin inhibitor in combination with restricting the caloric intake of the subject, thereby effecting an amelioration in abnormal metabolic indices of said subject.

Background of the Invention

The reduction of body weight and/or fat stores in man is of significant benefit, both cosmetically and physiologically. Whereas controlled diet and exercise can produce modest results in the reduction of weight and body fat deposits, these results are often unsatisfactory due to the substantial reduction in metabolic rate which accompanies a reduced calorie diet. Further, although a loss in body weight is seen with reduced caloric intake, this loss is often temporary and/or due to a reduction in lean body weight (as opposed to loss of fat). Various studies have shown that most calorie restriction diets result in weight loss approximately 40% of which is body fat lost and the remainder is lean body mass loss.

The reduction of body fat stores on a long term, or permanent basis in domestic animals is also obviously of considerable economic benefit to man, particularly since animals supply a major portion of man's diet; and the animal fat may end up as de novo fat deposits in man, with resulting adverse effects on health.

Obesity and insulin resistance, the latter of which is generally accompanied by hyperinsulinemia or hyperglycemia or both, are often associated conditions. No effective treatment has been found for controlling obesity-associated hyperinsulinemia or insulin resistance. Hyperinsulinemia is a higher-than-normal level of insulin in the blood. Insulin-resistance can be defined as a state in which a normal amount of insulin produces a subnormal biologic response. In insulin treated patients with diabetes, insulin resistance is considered to be present whenever the therapeutic dose of insulin exceeds the secretory rate of insulin in normal persons. Insulin resistance is also defined by higher-than-normal levels of insulin (i.e., hyperinsulinemia) when accompanied by normal or elevated levels of blood glucose. Despite decades of research on these serious health problems, the etiology of obesity and insulin resistance is unknown.

The principal unit of biological time measurement, the circadian or daily rhythm, is present at all levels of vertebrate and particularly mammalian organization. Daily rhythms have been reported for many hormones inclusive of the adrenal steroids. e.g., the glucocorticosteroids, notably cortisol, and prolactin, a hormone secreted by the pituitary. The peak concentration of prolactin occurs at different times of day in lean and fat animals. The physiological responses to an increase in circulating prolactin (e.g., prolactin injections) include increases and decreases in body fat stores, dependent on the time of day of the prolactin increase. Prolactin was thus found to stimulate fattening only when injected at certain times of the day. Furthermore, the type of response to prolactin and the time at which this response is elicited was found to differ between lean animals and fat animals.

In our prior co-pending patent application Ser. No. 192,332 we have disclosed and claimed methods for regulating lipid metabolism disorders by administering prolactin (or both prolactin and a glucocorticosteroid ("GC")) into the bloodstream of an animal or human on a timed daily basis in an amount and for a period of time sufficient to modify and reset the neural phase oscillation of the prolactin daily rhythm which then increases insulin sensitivity. The prolactin (or prolactin and glucocorticosteroid) injections are timed to create a peak in the subject's daily prolactin (or both prolactin and glucocorticosteroid) level profile that coincides in time with the peak prolactin level (or prolactin and GC peaks, respectively) of a lean, insulin-sensitive human to increase insulin sensitivity and reduce body fat stores. Injections of the same agent(s) are timed towards the peak prolactin level time of an obese subject to achieve fat gain, if desired.

In our co-pending prior application Ser. No. 463,327 we have disclosed and claimed a method of modifying and resetting the neural phase oscillations of the brain which control both prolactin and GC in an obese animal (or human) by administering a dopamine agonist at a predetermined time of day such that the prolactin (and/or GC) peak(s) of the obese animal (or human) will be phase-shifted to occur at the time that it occurs (they occur) in a lean animal (or human), with the result that at least one of body fat stores, body weight, hyperinsulinemia, or hyperglycemia will be reduced and/or insulin sensitivity will be increased.

In our co-pending prior application Ser. No. 719,745 we have disclosed and claimed enhanced methods for modifying and resetting the neural phase oscillations of the brain which control prolactin levels comprising both (a) administering to the subject a prolactin inhibitor (dopamine agonist) shortly after the time at which the normal prolactin profile peaks to reduce prolactin levels to the low "day" levels and (b) administering to the subject a prolactin stimulator at a time just before the prolactin level peaks in normal subjects with the objective of causing the subject's prolactin secretion profile to mimic in shape and time the profile of a lean human not suffering from one or more of the aforementioned metabolic disorders.

Ser. No. 719,745 also discloses and claims the further administration of a thyroid hormone to subjects that are being treated with the dopamine agonist and/or prolactin stimulator, especially to those subjects that are chronically or seasonally hypothyroid.

Our co-pending Ser. No. 995,292 discusses improved methods of detecting abnormal or aberrant prolactin level profiles of a subject, determining whether treatment is necessary, and if found necessary, methods of altering the prolactin level curves so that they more closely resemble those of a normal subject.

However, these methods of detecting, comparing, and adjusting prolactin level profiles have not been applied in combination with a reduced calorie diet. Significantly, this combination has now been found to have a synergistic effect on the improvement of one or more metabolic indices when compared to either the drug treatment or the diet treatment alone.

SUMMARY OF THE INVENTION

In one aspect, the present invention is directed to an improvement in a method of weight and/or body-fat reduction comprising a (preferably moderate) reduction in the caloric intake of a subject in need of such treatment in combination with administration to said subject of a prolactin inhibitor.

In another aspect, the present invention is directed to an improvement in a method for altering and/or resetting prolactin profiles (and thereby controlling one or more metabolic disorders such as obesity, excessive body fat, hyperlipidemia, hyperlipoproteinemia, hyperglycemia, hypercholesterolemia, hyperinsulinemia, insulin resistance, glucose intolerance, and Type II diabetes) comprising administration to a subject in need of such treatment of a prolactin inhibitor at a predetermined time or times during a 24-hour period in combination with a (preferably moderate) reduction of the caloric intake of said subject.

DETAILED DESCRIPTION OF THE INVENTION

All patents, patent applications and literature references cited herein are incorporated by reference in their entirety as if their disclosures were physically present in the present specification. In case of conflict, however, the present disclosure controls.

A reduction in caloric intake has long been used as an attempted treatment for obesity. However, it is well documented that reduction in caloric intake soon reduces metabolic rate, which causes weight loss to slow down and even stop. Furthermore, after the caloric reduction is discontinued and an unrestricted diet is resumed, the slower metabolic rate causes rapid weight gain. As a result, most attempts at weight control through caloric restriction are unsuccessful or only moderately successful and any benefit is short lived. In fact, often, the subject ends up weighing more than before the diet began. Additionally, a drastic calorie restriction (e.g. 50% of the pre-diet caloric intake) is generally required for weight loss.

Further, caloric restriction is known to favor loss in lean body mass rather than body fat, which significantly diminishes the health benefit of weight loss.

The administration of prolactin inhibitors at certain times of day has been shown to promote weight loss in animals, wherein most or all of the weight lost is in fact body fat. In humans, the administration of prolactin inhibitors at predetermined times of day (designed to cause the aberrant prolactin profile of the human to resemble a "normal" prolactin profile) has been shown to cause substantial fat loss even though there is minimal or no weight loss.

It has been discovered that by combining lowered caloric intake with the administration of prolactin inhibitors, as described below, the reduction in metabolic rate (as measured for example by oxygen consumption and $W_2$ production) can be reduced or avoided.

The combination of administration of prolactin inhibitors with diet also superadditively increases the loss of both body weight and body fat.

Figure 1:
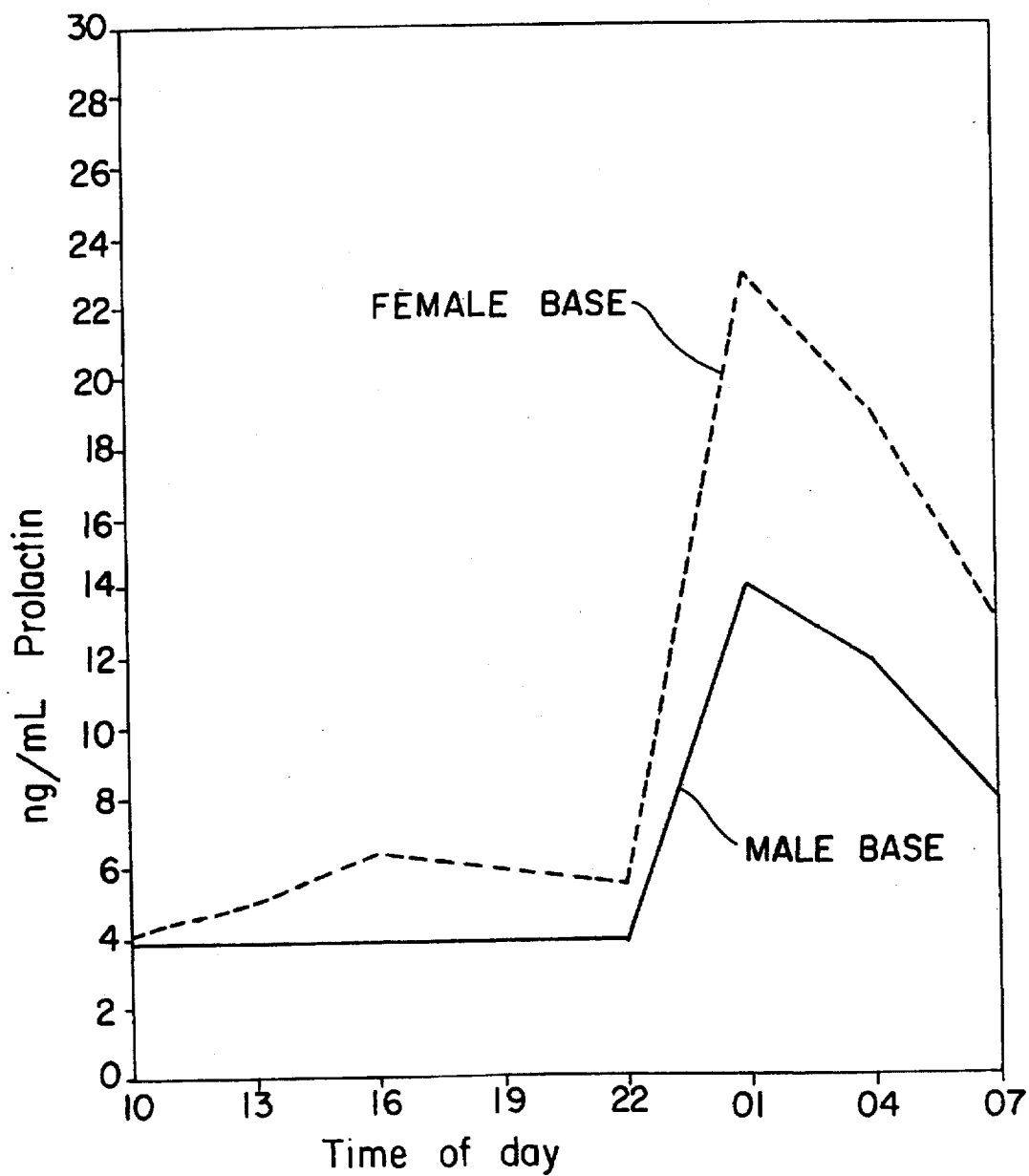
FIG. 1 is a plot of prolactin level v. time for healthy lean young males (tracing M) and females (tracing F) (hereafter referred to respectively as the male and female "normal" prolactin curves).

Further, through the previous work of the present inventors, it is known in the art that metabolic disorders such as obesity, hyperglycemia, hyperinsulinemia, hypercholesterolemia, hyperlipidemia and Type II diabetes are associated with aberrant patterns in the daily levels (and fluctuations) of prolactin. Healthy (normal) subjects, i.e., lean, young members of a species not suffering from such metabolic abnormalities (or other disorders such as congenital disorders, autoimmune disease or malignancies) have highly predictable daily prolactin level profiles, which in humans are characterized by a low and relatively constant prolactin level during the waking hours (day) followed by a sharp rise to a peak during sleep (night) and subsequent more gradual tapering down to the waking hours level by morning. See FIG. 1. Alteration of the aberrant prolactin profile of a subject by the timed administration of prolactin inhibitors synergistically improves one or more of the foregoing metabolic indices when the prolactin profile is altered and simultaneously the subject is placed on a moderately reduced calorie diet as compared with the differences seen with the prolactin inhibitor treatment alone.

In the present context "lean" means not obese and not abnormally underweight. In turn, an obese human is defined as a human whose body weight is over twenty percent above the ideal body weight for a given population (R. H. Williams, *Textbook of Endocrinology*, 1974, pp. 904–916). An abnormally underweight human is anyone at least 10% below his/her ideal bodyweight. Ideal body weight (IBW) can be determined by using the Metropolitan Life Insurance Company standard age/height/weight charts. An abnormally high body fat percentage is over 17% of body mass for men and over 25% for women.

Diet Aspect

According to the present method, the caloric content of diet of the subject being treated will preferably be reduced moderately (e.g., to 90%–70% of the caloric intake required for weight maintenance) but not to a starvation level. It is preferred that the subject consume 70% of the calories that the subject requires to maintain its initial weight, but the total caloric intake of the human subject should not be reduced below 1200 calories/day. Although any component of the diet can be reduced or eliminated to bring about this 30% reduction, it is preferred that reduction in fat be a significant portion of the eliminated calories. Further, it is preferred that the reduction in calories be relatively consistent for each meal, as opposed to the elimination of any one particular meal. A preferred diet is the diet recommended by and available from the American Diabetes Association, Alexandria Virginia (published in its 1986 *Guidelines*).

Prolactin Alteration Aspect

The alteration of prolactin levels conjoined to the aforementioned restriction of caloric intake is effected essentially as described in the prior co-pending applications of the same inventive entity, particularly Ser. No. 07/995,292. For convenience, these prolactin altering methods are summarized below.

A prolactin level profile of a subject is obtained at the commencement of the combined diet drug treatment, and is used to determine the timing of administration of the prolactin inhibitors. This may be done by collecting blood samples from the subject at timed intervals during a consecutive 24-hour time period (preferably at 3 hour intervals), assaying each blood sample for prolactin content, plotting the time of blood sampling against the quantity of prolactin present in each sample to generate a data point for each sample, and connecting the data points (or fitting them to a curve) to form the prolactin level curve of the subject. Details of this evaluation method are given in co-pending U.S. application Ser. No. 995,292. Briefly, a daytime prolactin profile is considered aberrant if at any time during the "day" the patient's prolactin level reaches a value more than 1 SEM higher than the corresponding value of the normal (Male or female as appropriate) prolactin curve. A nighttime prolactin profile is considered aberrant if at any point during "sleeptime" the prolactin level reaches a value more than 1 SEM lower than the corresponding value of the normal prolactin curve. "SEM" means standard deviation of the mean and is 1.0–2.0 ng/ml for male daytime and about 3.0 ng/ml for male night-time prolactin values; for females, 1 SEM is 1–3 ng/ml for daytime and 3–6 ng/ml for nighttime prolactin levels.

Although females generally have higher prolactin levels and sharper peaks than males, the shape of the normal prolactin profile for both sexes is qualitatively similar and does not vary appreciably from normal individual to normal individual (of the same sex) within the same species. See FIG. 1.

By contrast, individuals who suffer from one or more metabolic disorders, such as obesity (or Type II diabetes or hyperlipidemia or hyperinsulinemia or hyperglycemia or hypercholesterolemia, or impaired glucose tolerance or impaired insulin sensitivity), have aberrant (commonly highly aberrant) daily prolactin level profiles. These prolactin level profiles not only differ substantially from the norm but they can also differ from one another.

Figure 2:
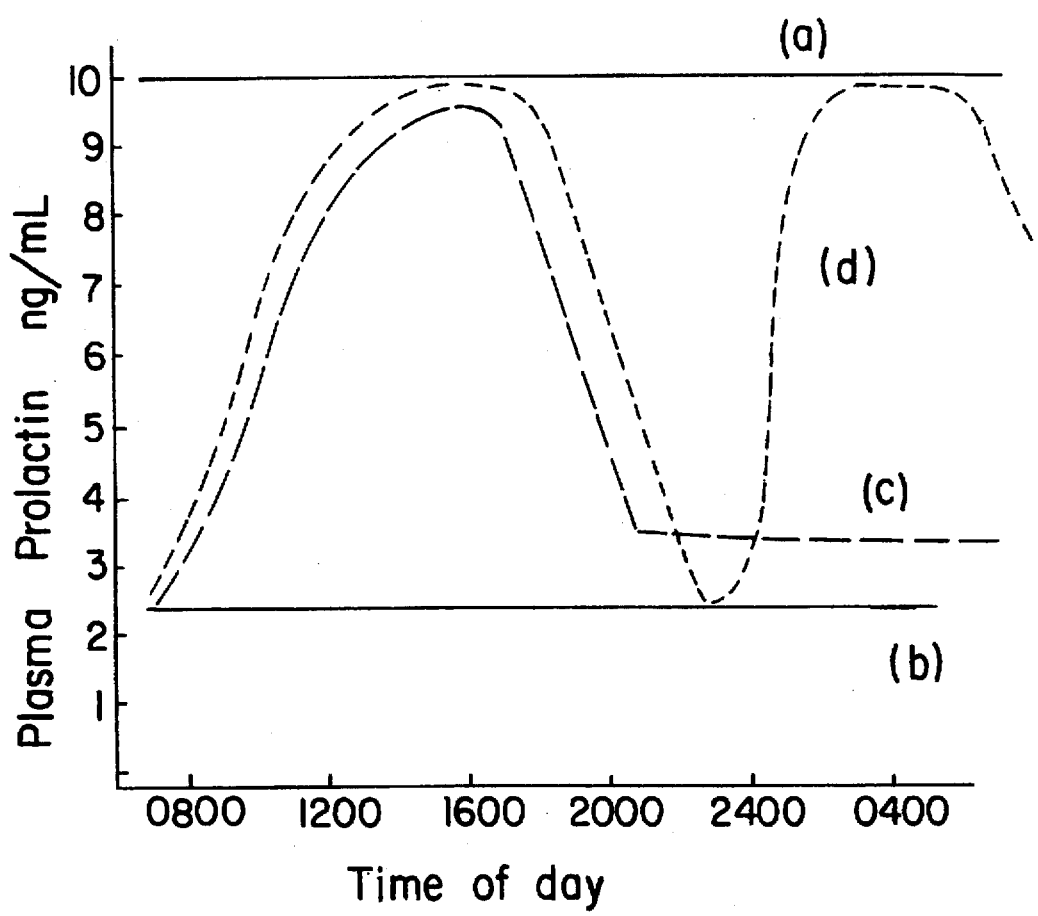
FIG. 2 is an illustrative superimposition of various types of typical human abnormal prolactin profiles identified by the letters (a) through (d), and described in more detail below.

The vast majority (at least about 80%) of patients with one or more of the foregoing metabolic disorders, have abnormal daily prolactin release profiles that fall generally in one of four patterns (FIG. 2):

(a) a relatively flat (peak-free) high level throughout the 24-hour period (in this context "high" means higher than the "day" or waking hours prolactin level);

(b) a relatively flat (peak-free) low level throughout the 24-hour period (in this context "low" means as low as or lower than the "day" or waking hours prolactin level);

(c) a peak during the "day" and a low level at "night" (in this context, "low" means low as compared to the normal average sleeptime prolactin value between 0100 and 0400); and (d) a peak during the "day" and a second peak at "night".

"Waking hours" or "day" means the period of time at which in normal (healthy) humans (not working night shifts or alternate shifts) prolactin levels are relatively invariant and low (between 07:00 h and 22:00 h).

As employed herein the term "sleeptime" or "night" means the period of time which in normal humans prolactin level rises to a peak (between 01:00 h and 04:00 h) and then tapers off.

The normal average prolactin levels between the hours of 01:00 h and 04:00 h are between 8.0 and 14.0 nanograms/ml for males and between 14.0 and 26.0 nanograms/ml for females.

"Prolactin inhibitor" shall include substances which directly or indirectly inhibit prolactin secretion in a subject (vertebrate animal or human). Nonlimiting examples of prolactin inhibitors include dopamine agonists such as dopamine and certain ergot-related prolactin-inhibiting compounds.

Nonlimiting examples of dopamine agonists are L-dopa, dopamine, 2-bromo-alpha-ergocriptine; 6-methyl-8beta-carbobenzyloxy-aminoethyl-10-alpha-ergoline; 8-acylaminoergolines, are 6-methyl-8-alpha-(N-acyl) amino-9-ergoline and 6-methyl-8 alpha-(N-phenylacetyl) amino-9-ergoline; ergocornine; 9,10-dihydroergocornine; and D-2-halo-6-alkyl-8-substituted ergolines, e.g., D-2-bromo-6-methyl-8-cyanomethylergoline. Moreover, the non-toxic salts of the prolactin-inhibiting ergot-related compounds formed from pharmaceutically acceptable acids are also useful in the practice of this invention. Bromocriptine, or 2-bromo-alpha-ergocryptine, has been found particularly useful in the practice of this invention.

According to the present method, the prolactin inhibitor is administered before it is needed and the administration is timed such that it produces its maximum effect on the daily prolactin level profile when it is needed the most. As a practical matter, however, there is some latitude on the time of administration of the prolactin inhibitor. Moreover, administration of prolactin inhibitors during sleep should be avoided.

The preferred prolactin inhibitor is bromocriptine. The average time for bromocriptine to exert its maximum prolactin inhibitory effect is between about 3 and about 4 hours after administration.

The following guidelines can be generally followed to initially determine bromocriptine administration timing based on the prolactin level profile determined for the subject:

If prolactin peaks between 07:00 and 10:00, bromocriptine will be administered at 07:00;

If prolactin peaks between 10:01 and 16:00, bromocriptine will be administered at 08:00;

If prolactin peaks between 16:01 and 19:00, bromocriptine will be administered at 09:00;

If prolactin peaks between 19:01 and 22:00, bromocriptine will be administered at 10:00;

If prolactin peaks between 22:01 and 01:00 bromocriptine will be administered at 10:00;

If there is a prolactin peak between 01:01 and 07:00 do not administer bromocriptine.

If prolactin does not peak but is too high, throughout waking hours, bromocriptine is administered at 07:00.

The time schedules given above are intended as guidelines for bromocriptine administration and those skilled in the art can adjust the precise timing of bromocriptine administration based on the actual prolactin profile of a patient to be treated.

The time at which a different prolactin inhibitory agent is to be administered to a patient can be determined by ascertaining the time between administration of the agent and the time at which the agent exerts its maximum biological (i.e., inhibitory) effect. The time at which an inhibitor has its maximum inhibition effect can be determined by administering the inhibitory drug to a patient with a known prolactin profile and then calculating the time that elapses between administration of the drug and exertion of the maximum effect on inhibition of the patient's (known) pre-treatment prolactin profile. Thereafter, the time of administration of the inhibitor to the patient is adjusted so that the drug is administered to the patient sufficiently in advance of the point at which the patient's prolactin curve has the greatest deviation from the normal profile so that it will provide maximum effect at the point (time) at which the patient's profile deviates most from the normal profile. In fine tuning a subject's medication administration schedule, the rebound effect that administration of a prolactin inhibitor during the day might have in sleeptime prolactin levels of this subject should be taken into account. In this manner the time of administration for a particular inhibitor can be determined using routine experimental procedures.

The precise time of prolactin inhibitor administration that will yield the most effective results in terms of efficacy of treatment in a given patient will depend upon the activity, pharmacokinetics, and bioavailability of a particular inhibitor, the physiological condition of the patient (including age, disease type and stage, physical condition, responsiveness to a given dosage and modulator), route of administration, etc. However, the above guidelines can be used as the basis for determining the optimum time of administration.

The foregoing are applicable for setting the initial therapy regimen. In general a patient receives between about 3 and about 100 micrograms of bromocriptine per kilogram of body weight per day, and preferably between about 10 and 40 micrograms per kg of body weight per day. The exact dosage of prolactin inhibitor required to achieve the optimum effect in terms of prolactin secretion adjustment must be adjusted for each patient based upon the patient's drug sensitivity (i.e., response to drug) age, disease state and stage and physical condition. The patient is periodically reevaluated by measuring prolactin levels at predetermined intervals during a 24-hour period, the first such reevaluation typically occurring at the end of four weeks from the onset of therapy, and subsequent reevaluations occurring every 4 to 8 weeks during therapy and then every 3 months thereafter.

Adjustments to the amount(s) of drug(s) administered and possibly to the time of administration may be made as described above based on these reevaluations.

Generally, adjustment of timing and amount of drug(s) is not considered necessary if the sleeptime prolactin peak during therapy is higher than normal as long as the peak value occurs at the right time, and the slopes of the peak are sharp (with normal values at each side of the normal peak).

The time at which it is desired to exert the maximum inhibitory effect on a particular patient (and therefore the appropriate time for administration) and the approximate amount (dosage range) for the degree of adjustment required can be determined by comparing the patient's abnormal (or reevaluation) prolactin profile with the standard profile.

In treating vertebrates, generally, dosages of the prolactin inhibitor (bromocriptine) are given, generally once a day, generally over a period ranging from about 10 days to about 180 days. The preferred prolactin inhibitor (bromocriptine) is given daily at dosage levels ranging from about 3 micrograms to about 100 micrograms, preferably from about 10 micrograms to about 40 micrograms, per kg. of body weight per day to modify, or alter, the prolactin profile and continued for a time sufficient to reset the circadian plasma prolactin rhythm.

In treating humans, the prolactin inhibitor (bromocriptine) is generally given at daily dosage levels ranging from about 3 micrograms to about 100 micrograms, preferably from about 10 micrograms to about 40 micrograms, per kg. of body weight. Such treatment is typically continued over a period of time ranging from about 10 days to usually about 180 days, resulting in modification and resetting of the lipid and glucose metabolism of the patient to that of a lean (i.e., normal) healthy person. For some patients (e.g. patients in particularly poor physical condition, or those of an advanced age) it may not be possible to reset their prolactin secretion profile within the above time periods and it is contemplated that such patients may require a longer, or even continuous, treatment with prolactin stimulators and/or inhibitors. The dosage and timing information set forth above is valid for bromocriptine but will probably have to be altered for other agents using the dosage and timing guidelines disclosed herein.

A prolactin-inhibiting compound is are administered daily to a subject preferably orally, or by subcutaneous, intravenous or intramuscular injection. Dermal delivery systems e.g., skin patches, as well as suppositories and other well-known systems for administration of pharmaceutical agents can also be employed.

A commonly preferred regimen for humans is to administer orally from 0.8 mg to 3.2 mg of bromocriptine per day in increments of 0.8 mg (i.e. 0.8, 1.6, 2.4 or 3.2 mg). (Preferred is a fast-release bromocriptine composition disclosed in patent application Serial No. 07/463,327, filed on Dec. 22, 1993 in the name of A. Cincotta, M. Cincotta, S. Tigner, et al.) The most common time of administration is within the period from 05:00 to 12:00. It is often desirable to administer part of the daily bromocriptine dosage (e.g. 0.8 or 1.6 mg) during the time interval 05:00–10:00 and the same or a different second dosage in late morning, e.g. within the interval of 09:00–13:00. This dosage and timing can be used with the combined diet/drug treatment of the present invention.

Body fat deposits, inclusive of adipose, arterial wall and plasma fat, of an obese person will be reduced, leveled out and generally maintained (after the treatments of the present invention are discontinued) at that of a normal (lean) person, over an extended period of time. A subject that exhibits the effects of insulin resistance, hyperlipidemia or hyperinsulinemia and/or hyperglycemia, or both insulin resistance and hyperinsulinemia and/or hyperglycemia, treated with the prolactin inhibitor at the appropriate times of day discussed above, will become more sensitive to insulin (i.e., will have a lower insulin resistance), and the effects of hyperinsulinemia and/or hyperglycemia and related abnormal metabolic values will be reduced on a long term basis. Treatment generally lasts between about 10 and about 180 days on average in humans, and preferably between about 90 and 180 days. The administration of the prolactin inhibitor in this manner will also reset the phase relations of the two neural oscillations and their various circadian expressions to alter metabolism on a long term basis (e.g., several years), if not permanently. In other words, the result of the timed daily dosages of the prolactin inhibitor will be a long term reversal of the major pathologies generally associated with obesity and/or Type II diabetes. Using the methods of the present invention, the levels of body weight, body fat stores, high plasma insulin concentrations, insulin resistance, hyperglycemia, hyperlipidemia and hypercholesterolemia, or all of these pathologies can be reduced on a long term basis by such treatment, or treatments, from the high levels often found in obese, hyperinsulinemic, hyperlipidemic and/or hyperglycemic persons to approach or conform to the much lower and much more desirable levels closer to or identical to those found in normal persons with normal metabolism and insulin levels. The foregoing effects are potentiated by the conjoined caloric restriction. Conversely, the effects of diet are potentialized by the conjoined timed prolactin inhibition.

The following are non-limiting working examples of therapy according to the present invention:

Clinical Results of the Combined Diet/Bromocriptine Treatment

The combined effects of diet and timed administration of bromocriptine were tested on a number of individuals who were obese or both obese and suffering from symptoms associated with obesity and/or Type II diabetes (such as impaired glucose tolerance, above normal glycosylated hemoglobin values, above normal triglyceride levels, above normal cholesterol). The individuals were divided into two groups: one group was given a placebo (at the same time as bromocriptine would have been administered if the subject had not been a control subject) and was placed on a 30% caloric restriction diet (based on the number of calories required for weight maintenance but taking the patient's eating habits into consideration). The recommended diet was the ADA diet. Meals were recommended to be taken regularly at 06:30–07:30 for breakfast; 12:00–13:00 for lunch and 17:30–18:30 for dinner. A snack could be had at 20:30–21:30. Another group was placed on the same diet and was also administered bromocriptine (from 0.8 mg up to 3.2 mg/day given orally between the hours of 05:00 and 13:00).

Compliance with the diet was monitored by interviewing each patient every two-three days and obtaining a list of the patient's food consumption. A prolactin profile was generated for each patient generally every four weeks during an 18-week period. The patient's body fat stores (by the pinch caliper method: 5 skinfolds for women; 7 skinfolds for men), fasting glucose, fasting insulin, fasting C-peptide, glycosylated hemoglobin, cholesterol and triglyceride levels were measured and oral glucose tolerance were also monitored at various intervals. Glycosylated hemoglobin was measured by HPLC, e.g., at the University of Texas Southwestern Medical Center, Diabetes Laboratory.

Persons who took bromocriptine and failed to comply with the diet served as positive controls.

After 18 weeks of treatment, typical results were as follows:

TABLE 1

| | WEIGHT (LBS) | | FAT (LBS) | |
|---|---|---|---|---|
| | Before | After | Before | After |
| GROUP I: DIET & BROMOCRIPTINE | | | | |
| P1 (F) | 171.25 | 146 | 63.7 | 44 |
| P2 (F) | 235 | 230 | 100.5 | 85.9 |
| P3 (F) | 293.5 | 269 | 137.7 | 109 |
| P4 (M) | 203.75 | 187.5 | 49.4 | 26 |
| P5 (M) | 294 | 275 | 69.1 | 51 |
| TOTAL | 1197.25 | 1107.05 | 430.4 | 315.9 |
| AVERAGE | 239 | 221.5 | 86.08 | 63.18 |
| Δ (Average) | | 17.5 | | 22.9 |
| GROUP II: BROMOCRIPTINE ONLY | | | | |
| P6 (M) | 236.5 | 234 | 61.1 | 50.8 |
| P7 (M) | 234.5 | 236 | 61.3 | 51.8 |
| TOTALS | 470.5 | 470 | 122.4 | 102.6 |
| AVERAGE | 235.37 | 235 | 61.2 | 51.3 |
| Δ (Average) | | 0.37 | | 9.9 |

TABLE 1-continued

| | WEIGHT (LBS) | | FAT (LBS) | |
|---|---|---|---|---|
| | Before | After | Before | After |
| GROUP III: DIET AND PLACEBO | | | | |
| P8 (M) | 255.75 | 218 | 85.3 | 61 |
| P9 (F) | 145 | 142.5 | 43.3 | 42.5 |
| P10 (F) | 280.25 | 275.75 | 126.5 | 121.5 |
| P11 (F) | 222 | 213 | 97.9 | 87.2 |
| P12 (M) | 238 | 234 | 53.4 | 42.7 |
| TOTALS | 1141 | 1083 | 406.4 | 354.9 |
| AVERAGE | 228.2 | 216.65 | 81.2 | 70.9 |
| Δ (Average) | | 11.55 | | 10.22 |
| AVERAGE W/O P8 | 221.31 | 216.25 | 80.3 | 73.5 |
| Δ (Average) W/O P8 | | 5 | | 6.8 |

The age, height, physical condition and drug regime of each patient are summarized below.

TABLE 2

| PATIENT CODE | AGE | HEIGHT (ft. in) | PHYSICAL CONDITION | BROMOCRIPTINE (mg) |
|---|---|---|---|---|
| P1 | 55 | 5.3 | 136% IBW | 2 weeks 1.6 @ 09:00 |
| | | | | Remainder 0.8 @ 05:00 |
| | | | | 1.6 @ 10:00 |
| P2 | 46 | 5.6 | 156% IBW; high cholesterol | 4 weeks 1.6 @ 09:00 |
| | | | | 4 weeks 0.8 @ 05:00 & 1.6 @ 10:00 |
| | | | | Remainder 1.6 @ 05:00 & 0.8 @ 10:00 |
| P3 | 39 | 5.9 | 200% IBW; high cholesterol | 2 weeks 0.8 @ 05:00 & 0.8 @ 09:30 |
| | | | | 4 weeks 0.8 @ 05:00 & 0.8 @ 08:30 |
| | | | | 4 weeks 0.8 @ 05:00 & 0.8 @ 09:30 |
| | | | | Remainder 1.6 @ 05:00 & 0.8 @ 10:00 |
| P4 | 53 | 5.6 | 130% IBW; high GHB and high fasting glucose | 4 weeks 1.6 @ 08:30 |
| | | | | 0.8 @ 05:00 & 0.8 @ 10:00 |
| | | | | Remainder 0.8 @ 05:00 & 0.8 @ 09:00 |
| P5 | 52 | 5.10 | 191% IBW; high GHB and high fasting glucose | 2 weeks 0.8 @ 05:00 |
| | | | | 0.8 @ 10:00 |
| | | | | 4 weeks 0.8 @ 05:00 |
| | | | | 0.8 @ 09:00 |
| | | | | Remainder 0.8 @ 05:00 |
| | | | | 0.8 @ 10:00 |
| P6 | 45 | 6 | 152% IBW; high cholesterol and triglycerides | 2 weeks 0.8 @ 05:00 & 0.8 @ 09:30 |
| | | | | 4 weeks 0.8 @ 05:00 |
| | | | | 0.8 @ 10:00 |
| | | | | Remainder 1.6 @ 05:00 |
| | | | | 0.8 @ 10:00 |
| P7 | 50 | 5.9 | 154% IBW; impaired glucose tolerance | 4 weeks 0.8 @ 09:00 |
| | | | | 4 weeks 0.8 @ 05:00 & 0.8 @ 10:30 |
| | | | | Remainder 1.6 @ 05:00 |
| P8 | 54 | 5.9 | 155% IBW; high cholesterol | N/A |
| P9 | 58 | 5.6 | 113% IBW; high cholesterol | N/A |
| P10 | 41 | 5.4 | 195% IBW; high cholesterol | N/A |
| P11 | 54 | 5.3 | 158% IBW; high fasting glucose and GHB | N/A |

TABLE 2-continued

| PATIENT CODE | AGE | HEIGHT (ft. in) | PHYSICAL CONDITION | BROMOCRIPTINE (mg) |
|---|---|---|---|---|
| P12 | 46 | 6 | 135% IBW; high GHB and high fasting glucose | N/A |

From Table 1, it can be seen that both the weight and fat loss were superadditively higher in subjects on the combined bromocriptine/diet regimen. Although the number of patients and controls is small, there are several aspects of this study that make this trend significant.

First, although the number of subjects on bromocriptine only was small in Table 1, the results (no appreciable weight loss, fat loss of about 10 lbs.) are closely comparable to those obtained in several prior studies. See, e.g. Cincotta et al. *Experientia*, 1987, 43: 416–417.

Second, turning to the subjects on placebo and diet in Table 1, the present inventors are of the opinion that the data for patient P8 should not be used to calculate averages because this individual appears to have lost an unusually high amount of both body weight and body fat which is inconsistent with all the other subjects. (The rest of the subjects in the placebo group lost pounds of weight and body fat within the range expected by prior studies.)

Third, all of the subjects were told to use the ADA diet, and were closely monitored which means they almost certainly consumed a much healthier diet than before they entered the study. This would bias the results adversely to the present invention.

Amelioration of the metabolic parameters described above was consistent with the body weight and body fat loss shown in Table 1. Most noteworthy are improvements achieved in glucose tolerance increase, insulin sensitivity increase, and glycosylated hemoglobin reduction.

We claim:

1. A method for reducing weight in a patient in need of such treatment comprising in combination the steps of:
   (a) administering daily to said patient a predetermined amount of a prolactin inhibitor confined to a first predetermined time; and
   (b) restricting said patient's daily caloric intake.

2. The method as recited in claim 1 wherein said prolactin inhibitor comprises a dopamine agonist.

3. The method of claim 2 wherein said dopamine agonist is bromocriptine.

4. The method of claim 3 wherein said predetermined amount is within the range of 0.8 to 3.2 mg of bromocriptine.

5. The method of claim 1 wherein said prolactin administration and caloric intake restriction continue for a period of time from about 10 to about 180 days.

6. The method of claim 1 wherein said predetermined time is within the period from 0500 to 1300 hours.

7. The method of claim 1 wherein a second predetermined amount of a prolactin inhibitor is given to said patient at a second predetermined time wherein said second predetermined time is within the period from 0900 to 1300 hours and said first predetermined time is within the period from 0500 to 1000 hours.

8. The method of claim 1 wherein said restriction in caloric intake is moderate.

9. The method of claim 1 wherein the caloric intake of said patient after said restriction is from 70 to 90% of the number of calories required by said patient for weight maintenance.

10. The method of claim 9 wherein the caloric intake of said patient after said restriction is 70% of the number of calories required for weight maintenance, provided that the restricted caloric intake is not below 1200 calories per day.

11. The method of claim 1 wherein said reduction in body weight persists for an extended period of time after cessation of said treatment.

12. A method for reducing body fat in a patient in need of such treatment comprising in combination the steps of:
   (a) administering daily to said patient a predetermined amount of a prolactin inhibitor confined to a first predetermined time; and
   (b) restricting said patient's daily caloric intake.

13. The method as recited in claim 12 wherein said prolactin inhibitor comprises a dopamine agonist.

14. The method of claim 13 wherein said dopamine agonist is bromocriptine.

15. The method of claim 14 wherein said predetermined amount is within the range of 0.8 to 3.2 mg of bromocriptine.

16. The method of claim 12 wherein said prolactin administration and caloric intake restriction continue for a period of time from about 10 to about 180 days.

17. The method of claim 12 wherein said predetermined time is within the period from 0500 to 1300 hours.

18. The method of claim 12 wherein a second predetermined amount of a prolactin inhibitor is given to said patient at a second predetermined time wherein said second predetermined time is within the period from 0900 to 1300 hours and said first predetermined time is within the period from 0500 to 1000 hours.

19. The method of claim 12 wherein said restriction in caloric intake is moderate.

20. The method of claim 12 wherein the caloric intake of said patient after said restriction is from 70 to 90% of the number of calories required by said patient for weight maintenance.

21. The method of claim 20 wherein said caloric intake of the patient after said restriction is 70% of the number of calories required for weight maintenance, provided that the restricted caloric intake is not below 1200 calories per day.

22. The method of claim 12 wherein said reduction in body fat persists for an extended period of time after cessation of said treatment.

23. A method for increasing the efficiency of weight reduction in a patient in need of such treatment comprising in combination the steps of:
   (a) administering daily to said patient a predetermined amount of a prolactin inhibitor confined to a first predetermined time; and
   (b) restricting said patient's daily caloric intake;
   said combination achieving an increased efficiency of weight reduction as compared to that achieved by either step (a) or step (b) alone; and thereby curbing or avoiding the metabolic rate decrease that accompanies dietary caloric restriction.

24. The method as recited in claim 23 wherein said prolactin inhibitor comprises a dopamine agonist.

25. A method for increasing body fat reduction in a patient in need of such treatment comprising in combination the steps of:
   (a) administering daily to said patient a predetermined amount of a prolactin inhibitor confined to a first predetermined time; and
   (b) restricting said patient's daily caloric intake;
   said combination achieving an increased efficiency of body fat reduction as compared to that achieved by either step (a) or step (b) alone: and thereby curbing or avoiding loss of lean body mass that accompanies dietary caloric restriction.

26. The method as recited in claim 25 wherein said prolactin inhibitor comprises a dopamine agonist.

27. A method for reducing weight in a patient in need of such treatment comprising in combination the steps of:
  (a) administering daily to said patient a predetermined amount of a prolactin inhibitor confined to a first predetermined time; and
  (b) restricting said patient's daily caloric intake such that the caloric intake of said patient after said restriction is from 70 to 90% of said patient's daily caloric intake prior to restriction, provided that the restricted caloric intake is not below 1200 calories per day.

28. The method as recited in claim 27 wherein said prolactin inhibitor comprises a dopamine agonist.

29. The method as recited in claim 28 wherein said dopamine agonist is bromocriptine.

30. A method for reducing fat in a patient in need of such treatment comprising in combination the steps of:
  (a) administering daily to said patient a predetermined amount of a prolactin inhibitor confined to a first predetermined time; and
  (b) restricting said patient's daily caloric intake such that the caloric intake of said patient after said restriction is from 70 to 90% of said patient's daily caloric intake prior to restriction, provided that the restricted caloric intake is not below 1200 calories per day.

31. The method as recited in claim 30 wherein said prolactin inhibitor comprises a dopamine agonist.

32. The method as recited in claim 31 wherein said dopamine agonist is bromocriptine.

* * * * *